United States Patent [19]

Goldman

[11] Patent Number: 4,836,373
[45] Date of Patent: Jun. 6, 1989

[54] HYPODERMIC SYRINGE AND COVER HANDLING DEVICE

[76] Inventor: Boris Goldman, 20 Gail Rd., Farmington, Conn. 06032

[21] Appl. No.: 251,777

[22] Filed: Oct. 3, 1988

[51] Int. Cl.⁴ .......................................... B65D 83/10
[52] U.S. Cl. ................................................ 206/366
[58] Field of Search ............................. 206/365, 366

[56] References Cited

U.S. PATENT DOCUMENTS

| | | | |
|---|---|---|---|
| 3,255,873 | 6/1966 | Speelman | 206/366 |
| 3,292,776 | 12/1966 | Penn | 206/366 |
| 3,367,486 | 2/1968 | Larson et al. | 206/366 |
| 3,876,067 | 4/1975 | Schwarz | 206/205 |
| 4,332,323 | 6/1982 | Reenstierna | 206/365 |
| 4,351,434 | 9/1982 | Elisha | 206/366 |
| 4,485,918 | 12/1984 | Mayer | 206/366 |
| 4,667,821 | 5/1987 | Shillington | 206/366 |

*Primary Examiner*—Joseph Man-Fu Moy
*Attorney, Agent, or Firm*—Richard A. Craig

[57] ABSTRACT

A device for handling a hypodermic syringe and a cover therefor has a base, a tubular body projecting from the base and having an open end for receiving a syringe cover and frictionally engaging the same. The device also has a mechanism for breaking the frictional engagement. The base has a piece of material one side of which adhesively engages the base. The other side of the piece of material has pressure sensitive material, so that the device is mountable on a plane surface. Only one hand is needed to operate the device, and a plurality of the devices can readily be arranged in an array in close proximity to each other.

9 Claims, 2 Drawing Sheets

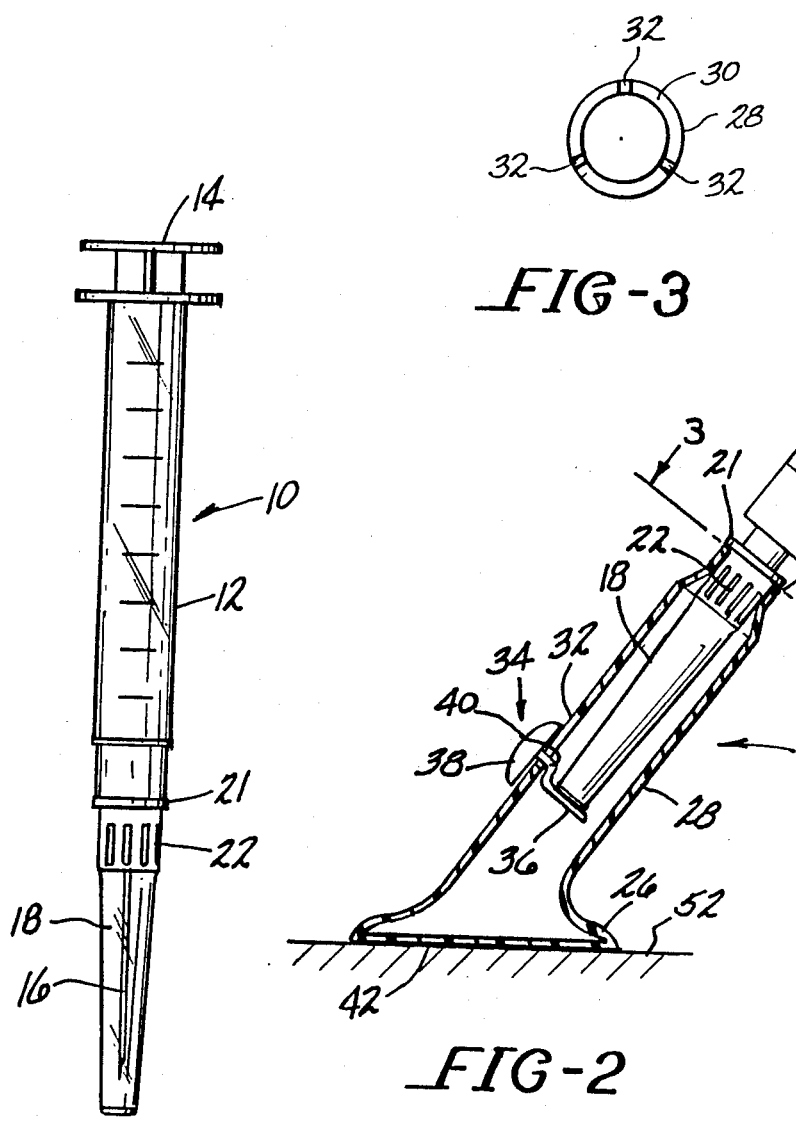

HYPODERMIC SYRINGE AND COVER HANDLING DEVICE

BACKGROUND OF THE INVENTION

This invention relates to a device for handling a hypodermic syringe and more particularly for holding a cover for a syringe in position to receive therein a needle of a hypodermic syringe and for holding the syringe assembled with its cover and for delivering the syringe with the cover thereon when desired, all with the use of only one hand which does not touch the needle.

The general subject of the invention has in the past few years assumed an increasing amount of attention because of ever increasing danger to medical personnel when they accidentally stick themselves with needles of hypodermic syringes.

Schwarz U.S. Pat. No. 3,876,067, issued Apr. 8, 1975 presents a collection box for pulling syringes off of needles.

Reenstierna U.S. Pat. No. 4,332,323, issued June 1, 1982 discloses a destruction device for hypodermic needles.

Elisha U.S. Pat. No. 4,351,434, issued Sept. 28, 1982 teaches a device for drawing needles off of syringes.

Mayer U.S. Pat. No. 4,485,918, issued Dec. 4, 1984 discloses needle disposal apparatus for preventing accidental needle sticks which occur when a technician attempts to return a used needle to a sheath, i.e., cover, prior to disposal. A hand-held funnel-like member supports a sheath during a sheathing operation, at the conclusion of which the sheathed needle is inside of a sealed container which, when full, is disposed of.

Shillington U.S. Pat. No. 4,667,821, issued May 26, 1987 teaches a closure device for unscrewing a needle from a syringe body.

It is an important object of the present invention to provide a hypodermic syringe handling device which holds a cover in position to receive therein a needle of a hypodermic syringe and holds the syringe with its needle assembled with its cover and delivers the syringe with the cover thereon when desired, and wich does all of the foregoing with the use of only one of the doctor's, nurse's or technician's hands which does not touch the needle.

It is another object of the present invention to provide such a device which is cheap in construction and simple and reliable in operation.

It is a further object of the present invention to provide an array of such hypodermic syringe handling devices.

The foregoing and other objects and advantages of the present invention will become apparent hereinafter.

SUMMARY OF THE INVENTION

The inventive device for handling a hypodermic syringe and a syringe cover includes a base, a tubular body projecting from the base to an open end for receiving and frictionally engaging the cover, and a longitudinal slot through the wall of the body. An expelling member has a shelf portion within the body, a knob portion outside the body and an intermediate portion rigidly joining the shelf portion and the knob portion and passing through the slot. The shelf portion is between the base and the open end and is movable toward the open end by thumb or finger force applied to the knob portion in the direction away from the base for engaging the cover to break the frictional engagement between the cover and the body, permitting withdrawal from the tubular body of the cover, with or without a syringe assembled therewith.

DESCRIPTION OF THE DRAWING

FIG. 1 is an elevational view of a typical hypodermic syringe assembled with a typical cover;

FIG. 2 is an assembled view showing substantially in axial section a hypodermic syringe and cover handling device which is a preferred embodiment of the invention, a hypodermic syringe cover and a hypodermic syringe, the latter being shown fragmentarily;

FIG. 3 is an enlarged view of the hypodermic syringe and cover handling device, taken on line 3—3 of FIG. 2.

DESCRIPTION OF THE INVENTION

Figure 4:
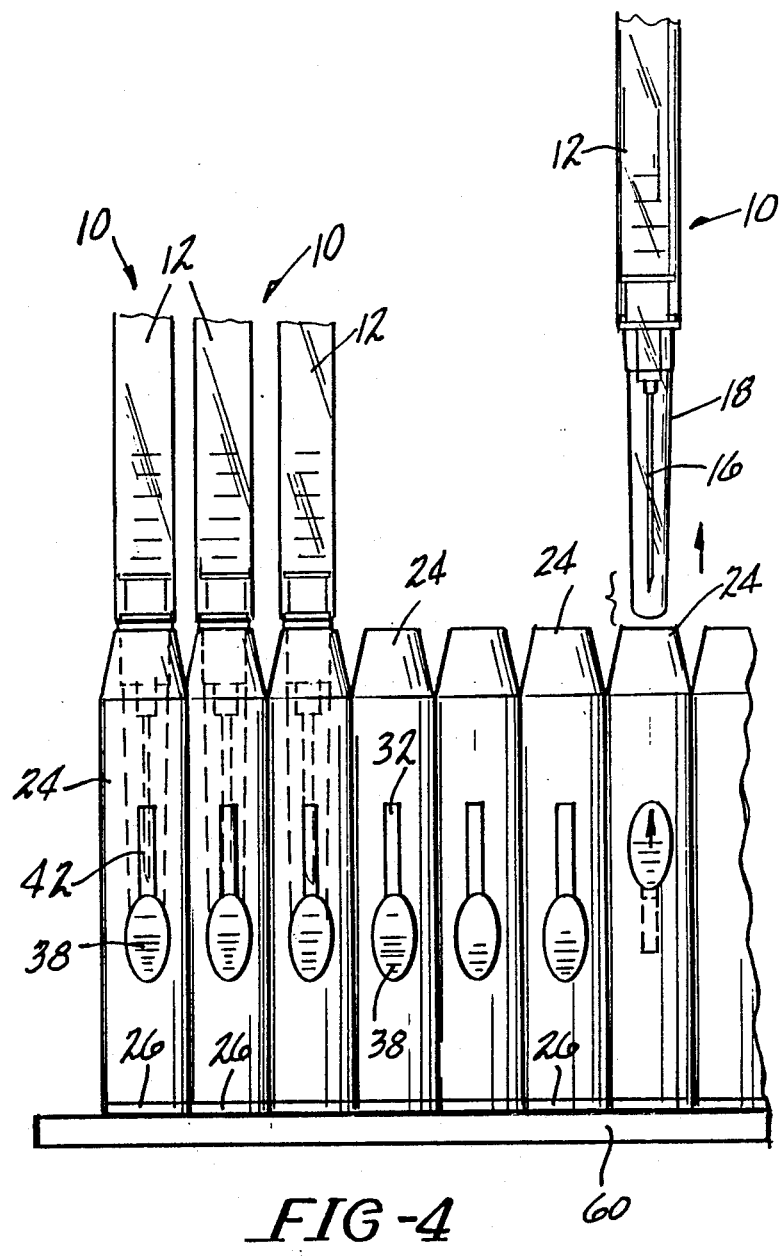
FIG. 4 is a partly schematic view showing an array of hypodermic syringe handling devices according to FIG. 2, and, fragmentarily, several syringes including a syringe with a cover thereon.

FIG. 1 shows an assembly of a typical hypodermic syringe 10 comprising a generally cylindrical plastic body member 12, a plastic plunger member 14 and a hypodermic needle 16 and a plastic cover 18 for needle 16. Cover 18, which has a closed end and an open end, is impositively held in place by frictional engagement of its open end on external axial splines 20 on the end of body member 12 adjacent needle 16. Cover 18 may have external splines 22 at the portion of cover 18 adjacent its open end which are at the same axial location as external splines 20 when cover 18 is installed on syringe 10. At its open end, cover 18 has an external circumferential external flange 21.

The invention will be described at first with particular reference to FIG. 2, which shows a preferred hypodermic syringe and cover handling device 24 comprising a flat bottomed base 26 and, extending upwardly therefrom, a plastic tubular body 28 having an axis which is disposed at an acute angle with respect to the flat bottom of base 26. As stated hereinafter, base 26 is provided with adhesive whereby device 24 can be readily mounted on a plane surface. The acute angle is shown as being on the order of about 60 degrees. Body 28 has an upper open end 30 its inside and outside diameters are substantially unchanged throughout most of its length but constrict to smaller size at and near open end 30. Also, as seen in FIG. 3, body 28 may be provided with a plurality of axial slots 32 opening at open end 30 whereby the portions of body 28 at free end 30 circumferentially adjacent between slots 32 are radially resiliently flexible. These resiliently flexible portions are capable of resiliently and frictionally receiving and gripping the portion of cover 18 adjacent its open end, i.e., splines 22 if present. External cover flange 21 limits the depth of insertion of cover 18 into body 28 by engaging free end 30 of body 28. A straight longitudinal slot 32 of limited length extends through the wall of body 28, for a purpose described below.

Base 26 and body 28 are preferably provided by a single piece of molded plastic material with an imperforate seamless juncture therebetween.

Hypodermic syringe and cover handling device 24 has an expelling member 34 for driving cover 18 out of frictional engagement with body 28. Expelling member 34 includes a shelf portion 36 within a body 28, a knob portion 38 outside body 28 and an intermediate portion 40 rigidly joining shelf portion 36 and knob portion 38 and passing through slot 32. Shelf portion 36 is between base 26 and open end 30 and is movable toward open end 30 by thumb or finger force applied to knob portion 38 in the direction away from base 26 for engaging cover 18 to break the frictional engagement between cover 18 and body 28.

Base 26 of hypodermic syringe and cover handling device 24 is provided on its underside with a piece of material 42 having pressure sensitive adhesive on both sides. One side is stuck to base 26 and the other side is initially covered with a piece of release paper (not shown) which is removable so that device 24 may be stuck to any convenient plane surface, such as that provided by horizontal member 52 (FIG. 2). Device 24 can just as easily be stuck to a vertical surface. When device 24 is applied to horizontal member 52, body 28 will be tipped about 30 degrees off vertical, since, as mentioned above, the axis of body member 28 is disposed at an angle of about 60 degrees with respect to base 26. It should also be mentioned that longitudinal slot 32 in the wall of body 28 is so oriented with respect to base 26 as to be on the upwardly facing surface of body 28 when device 24 is mounted (i.e. stuck) on horizontal surface 52. Thus, knob portion 38 is conveniently available.

When device 24 is mounted on horizontal surface 52, a cover 18 (either assembled with syringe 10 or not) may be inserted by one hand, closed end first, into open end 30 of body member 28, until flange 21 engages open end 30 of body 28, as shown in FIG. 2. At the conclusion of this insertion, cover 18 will frictionally engage member 28, and expelling member 34 will be at a relatively low position with respect to slot 32, as shown in FIG. 2, with the closed end of cover 18 confronting shelf portion 36. Syringe 10 with its needle 16 unsheathed can then be removed with cover 18 remaining firmly in body member 28.

Syringe 10 may thereafter be inserted by one hand into cover 18, which is held by device 24 in convenient position to receive same, and knob portion 38 may be manipulated as described above to raise shelf portion 36 to engage cover 18 to break the frictional engagement between cover 18 and body member 28.

It is to be noted that it is not necessary that shelf portion 36 engage cover 18 when cover 18 is fully inserted into body 28. The bottom end of slot 32 may be sufficiently close to base 26 that there is no such engagement. Thus, device 24 can be used with covers 18 of different lengths.

FIG. 4 shows an array of hypodermic syringe and cover handling devices 24 mounted in close proximity to each other on a horizontal member 60. Syringes 10 are shown assembled with a few devices 24 and one syringe 10 is shown just after having been removed from one device 24.

It is apparent that the invention attains the stated objects and advantages and others.

The disclosed details are exemplary only and are not to be taken as limitations on the invention except as those details are included in the appended claims.

What is claimed is:

1. A device for handling a hypodermic syringe and a syringe cover, said device comprising a base, a tubular body projecting from said base to an open end for receiving and frictionally engaging the cover, and a longitudinal slot through the wall of said body, and an expelling member having a shelf portion within said body, a knob portion outside said body and an intermediate portion rigidly joining said shelf portion and said knob portion and passing through said slot, said shelf portion being between said base and said open end is movable toward said open end by thumb or finger force applied to said knob portion in the direction away from said base for engaging the cover to break the frictional engagement between the cover and said body.

2. A device according to claim 1 wherein said base is provided with a piece of material one side of which is in adhesive engagement with said base and having pressure sensitive adhesive on the other side for mounting said device on a plane surface.

3. A device according the claim 1 wherein said base is flat and the axis of said body makes an acute angle with respect to said base.

4. A device according to claim 3 wherein said acute angle is on the order of about 60 degrees.

5. A device according to claim 1 wherein said body has a plurality of spaced axial slots opening at said open end, whereby the portions of said body between said spaced slots are radially resiliently flexible for facilitating the frictional engagement with the cover.

6. A device according to claim 1 wherein said base and said body are provided by a single piece of plastic material.

7. A device according to claim 6 wherein the bottom of said base is flat and the axis of said body makes an acute angle with respect to said base and said longitudinal slot is so oriented with respect to said base as to be upwardly facing when said device is mounted on a horizontal surface.

8. A device according to claim 7 wherein said acute angle is on the order of about 60 degrees.

9. A plurality of devices according to claim 1 arranged in an array in close proximity to each other.

* * * * *